(12) United States Patent
Ingham et al.

(10) Patent No.: US 9,658,352 B2
(45) Date of Patent: May 23, 2017

(54) METHOD OF MAKING A STANDARD

(71) Applicant: PANalytical B.V., Almelo (NL)

(72) Inventors: Mark Ingham, Nottinghamshire (GB); Leian Grimsley, Nottinghamshire (GB)

(73) Assignee: PANALYTICAL B.V., Almelo (NL)

( * ) Notice: Subject to any disclaimer, the term of this patent is extended or adjusted under 35 U.S.C. 154(b) by 111 days.

(21) Appl. No.: 14/593,712

(22) Filed: Jan. 9, 2015

(65) Prior Publication Data

US 2015/0198727 A1 Jul. 16, 2015

(30) Foreign Application Priority Data

Jan. 13, 2014 (EP) ..................... 14151007

(51) Int. Cl.
*G01N 23/22* (2006.01)
*G01T 7/00* (2006.01)
*G01N 23/223* (2006.01)

(52) U.S. Cl.
CPC .......... *G01T 7/005* (2013.01); *G01N 23/223* (2013.01); *G01N 2223/303* (2013.01); *G01N 2223/3037* (2013.01)

(58) Field of Classification Search
CPC ......... G01N 2223/3037; G01N 23/223; G01N 2223/303; G01T 7/005
See application file for complete search history.

(56) References Cited

U.S. PATENT DOCUMENTS

| 4,991,191 | A | 2/1991 | Suryanarayanan | |
|---|---|---|---|---|
| 2008/0233652 | A1* | 9/2008 | Kreyenschmidt | G01N 21/278 436/8 |
| 2011/0007869 | A1* | 1/2011 | Gendreau | G01N 23/20 378/46 |
| 2015/0023467 | A1* | 1/2015 | Birnbaum | G01N 23/2204 378/47 |

FOREIGN PATENT DOCUMENTS

| CN | 101 799 437 | | 12/2011 | |
|---|---|---|---|---|
| JP | 2009 031072 | | 2/2009 | |
| JP | 2009031072 | A * | 12/2009 | .............. G01N 1/36 |

OTHER PUBLICATIONS

Dargie, M., "Optimized sample preparation procedures for the analysis of solid materials by total-reflection XRF" Fresenius' Journal of Analytical Chemistry, 1997, vol. 357, No. 6, p. 589-593.*
Billiet, J., et al. "Multielement thin film standards for XRF analysis", X-Ray Spectrometry vol. 9, No. 4, Oct. 1, 1980, pp. 206-211.*
Śliwiński, Maciej G., et al. "Making low concentration in-house pressed pellet trace element standards for carbonate rock analyses by WD-XRF." Chemical Geology 298 (2012): 97-115.*
ICP Standard Making Protocol, retrieved from soils.cals.uidaho.edu/icp/ICP_standards.htm (Aug. 29, 2003).*

(Continued)

*Primary Examiner* — Wyatt Stoffa
(74) *Attorney, Agent, or Firm* — Leason Ellis LLP

(57) ABSTRACT

A measurement standard suitable for measuring amounts of certain elements in pharmaceutical excipients is described. A reference standard is dissolved in a solvent, for example acetone, and mixed with a pharmaceutical excipient such as cellulose, lactose or calcium carbonate. The solvent is then evaporated to provide a dry standard.

7 Claims, 1 Drawing Sheet

(56) References Cited

OTHER PUBLICATIONS

J. Billiet et al: Multielement thin film standards for XRF analysis, X-Ray Spectrometry, vol. 9, No. 4, Oct. 1, 1980 (Oct. 1, 1980), pp. 206-211, XP055117631, ISSN: 0049-8246, DOI: 10.1002/xrs.1300090412 * the whole document *.

"Benecel Hypromellose (HPMC) and Methylcellulose (MC)—Low Viscosity Grades", Ashland Ashland Catalogue, Apr. 3, 2013 (Apr. 3, 2013), pp. 1-7, XP002724436, document PC__10370__Benecel__HPMC__MC.pdf from the ashland.com/Ashland/Static/Documents/ASI/ website. [retrieved on May 13, 2014] * p. 4 *.

Yasuhiro Shibata et al: "X-ray fluorescence analysis of Cr, As, Se, Cd, Hg, and Pb in soil using pressed powder pellet and loose powder methods", X-Ray Spectrometry, vol. 38, No. 5, Sep. 1, 2009 (Sep. 1, 2009), pp. 410-416, XP055117674, ISSN: 0049-8246, DOI: 10.1002/xrs.1195 * abstract * *Sections entitled 'Soil samples', 'Reagents' and 'Preparations of calibrating standards': p. 411, col. 1-col. 2 *.

V Natarajan et al: "Determination of uranium and thorium in zircon by energy dispersive X-ray fluorescence technique", Indian Journal of Chemical Technology, Nov. 1, 2012 (Nov. 1, 2012), pp. 399-402, XP055117513, document 123456789/15135/1/IJCT19(6)399-402.pdf from the nopr.niscair.res.in/bitstream/website [retrieved on May 12, 2014] * p. 400, col. 1, last paragraph-col. 2, paragraph 1 *.

Ian Campbell, et al, "The Use of EDXRF for Pharmaceutical Material Elemental Analysis", American Pharmaceutical Review (Nov. 9, 2012), which is presently available electronically at: http://www.americanpharmaceuticalreview.com/1504-White-Papers-Application-Notes/124874-The-Use-of-EDXRF-for-Pharmaceutical-Material-Elemental-Analysis/.

* cited by examiner

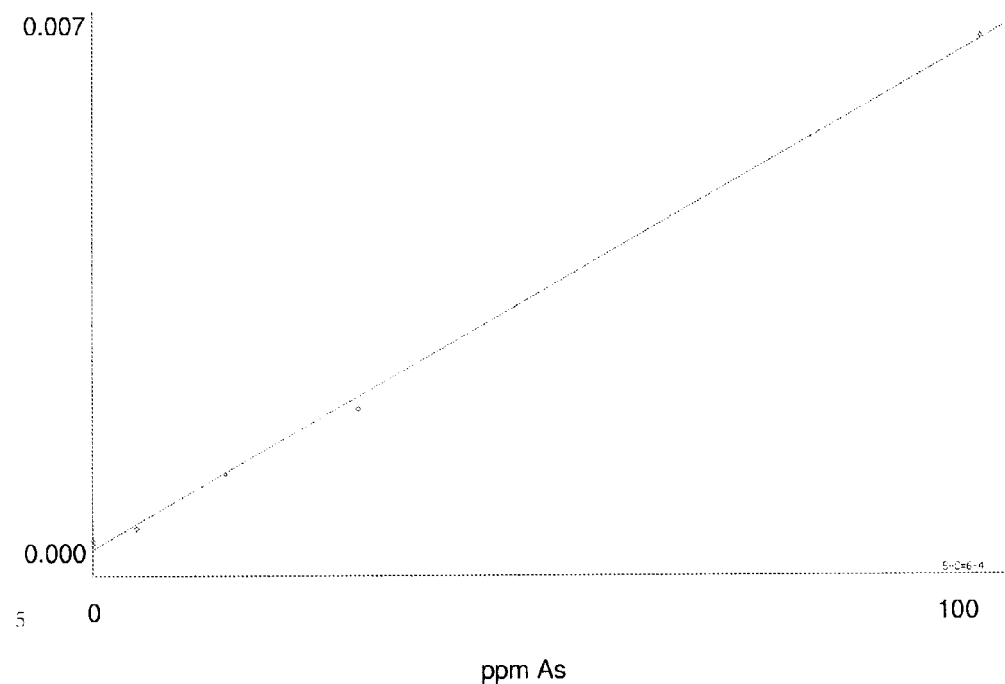

METHOD OF MAKING A STANDARD

CROSS-REFERENCE TO RELATED APPLICATIONS

The present application claims priority under 35 U.S.C. §119 to European Patent Application No. 14151007.3, filed Jan. 13, 2014, which is hereby incorporated by reference in its entirety.

FIELD OF INVENTION

The present invention relates to a method of making a standard and a standard made by the invention.

BACKGROUND TO THE INVENTION

X-ray fluorescence, XRF, is a technique widely used in some technical areas. X-rays are directed at a sample and secondary X-rays are emitted from the sample. The secondary X-rays are dependent on the elements contained in the sample and the intensity of the emitted X-rays can be used to determine the concentration of the element in the sample.

The intensities of emitted X-ray fluorescence are dependent not only on the concentration of the relevant element but also on the preparation of the sample and the matrix within which the element is contained. Sample preparation is accordingly important.

For accurate measurement, X-ray fluorescence apparatus needs to be calibrated against a suitable reference sample which should be similar to the sample being measured. Quantitative measurements can then be obtained by comparing the X-rays emitted from the reference sample and the test sample.

Reference samples/materials for many applications of XRF are commercially available. However, in order to use XRF in a wider range of commercial applications, including for example the pharmaceutical sector, there is a need for suitable reference samples.

The use of XRF for pharmaceuticals has been discussed by Ian Campbell, et al, "The Use of EDXRF for Pharmaceutical Material Elemental Analysis", American Pharmaceutical Review (2012), which is presently available electronically at: www.americanpharmaceuticalreview.com/1504-White-Papers-Application-Notes/124874-The-Use-of-EDXRF-for-Pharmaceutical-Material-Elemental-Analysis/-. This paper discusses the application of XRF in this sector.

The reference samples discussed in that paper are mentioned to be prepared using a cellulose excipient material as the matrix and using organometallics. In such a process, the starting point is a solution of the metal in the form of an organometallic dissolved in toluene.

However, preparing reliable standards in this way has proved to be difficult time consuming and potentially hazardous to health.

Further, suitable dry reference standards for pharmaceuticals are not available commercially.

The accurate measurement of elements, for example metallic elements in particular, may be required for a number of reasons. There may be a need to check that any elements that may have been involved in the manufacture of the pharmaceutical, for example as catalysts, are not present in the product. There may be a need to check that there is no contamination which could potentially occur in a number of ways. Such checks may be chosen by the manufacturer or required by national or international standards bodies responsible for health and/or safety.

Accordingly, there is a need for a way of preparing reference standards including a matrix of material typically used as a pharmaceutical excipient and for the standards produced by such a method.

SUMMARY OF THE INVENTION

According to a first aspect of the invention, there is provided a method of manufacturing a reference standard for X-ray fluorescence measurements, comprising:
  providing a reference sample having a known concentration of a predetermined element;
  transferring the reference sample volumetrically using a solvent;
  mixing with an excipient material;
  evaporating the solvent to form a dry reference sample with the known concentration of the metal homogeneously dispersed in the excipient material.

The reference sample may be an aqueous reference standard, i.e. the element carried in a water based solution such as water, dilute nitric acid or similar.

The solvent should be miscible with the reference sample having a known concentration of predetermined element. The solvent may be for example acetone, water, tetrahydrofuran, propan-1-ol, propan-2-ol, methanol, ethanol, 1-4 dioxane, dimethylsulfoxide, acetonnitrile or mixtures of these solvents.

Such solvents are suitable for mixing with most available aqueous reference standards for use with the invention. In particular, the solvent may be acetone which is widely available and which can readily be evaporated.

Alternative solvents may be other ketones, for example butanone, ethyl isopropyl ketone or methyl isobutyl ketone.

The excipient material may be lactose, cellulose or calcium carbonate, any mixture of the three or similar material.

The step of evaporating the solvent may include carrying out a first evaporation step at room temperature followed by a second evaporation step in an oven at an elevated temperature above 35° C. The second evaporation step may be carried out for a period of at least 24 hours.

The method may provide a reference sample having a known concentration of a plurality of elements.

The method may further involve providing a plurality of dry reference standards having different known concentrations of the predetermined element. In this case, the step of transferring the reference sample volumetrically into a solvent for the plurality of dry reference standards may be carried out by transferring a different concentration of the reference sample volumetrically into a respective solvent for each of the plurality of dry reference standards to obtain the plurality of dry reference standards with different known concentrations of the predetermined element.

In a second aspect of the invention, there is provided a method of calibrating X-ray fluorescence apparatus, comprising:
  preparing a plurality of reference samples having different concentrations of the predetermined element using a method as described above;
  measuring the X-ray fluorescence of each of the reference samples; and
  calculating a calibration line from the measured X-ray fluorescence and the known concentrations of the predetermined element.

A third aspect of the invention relates to a dry reference standard or a set of dry reference standards produced using the methods above.

Further developments of the invention are the subject-matter of the dependent claims.

BRIEF DESCRIPTION OF THE FIGURE

The FIGURE depicts a calibration line prepared using the standards. The line records the measured XRF intensity (I rate corrected As/Internal ratio) versus the known concentration of As in ppm.

DETAILED DESCRIPTION

In order to carry out XRF measurements on a pharmaceutical sample, a dry reference standard with an element distributed homogenously throughout the standard is required.

Elements supported in liquid, typically in solution, are commercially available as reference standards. For example, the standard may be a commercially available standard suitable for inductively coupled plasma optical emission spectrometry (ICP-OES), inductively coupled plasma mass spectrometry (ICP-MS), ion chromatography (IC), or atomic absorption spectrometry (AAS), standard solutions. One such standard is 10 000 ppm, (parts per million), Arsenic (As) in a 5% (volume-volume, v/v) nitric acid solution. It will be appreciated that 10 000 ppm is 1%. Other such standards are available for other elements of the periodic table.

To prepare a dry reference standard suitable for XRF measurements on a pharmaceutical, a reference standard containing a predetermined element supported in liquid is transferred volumetrically into a solvent, for example acetone. The resulting diluted reference standard contains a more dilute concentration of the predetermined element, for example in the range 10 to 500 ppm.

A matrix material corresponding to the matrix of the sample to be tested is provided in powder form. The material may be a material used as a pharmaceutical excipient and may typically be calcium carbonate, cellulose or lactose.

The volume of the diluted reference standard in a solvent is then mixed with a known mass of the powder to form a mixture. The mixture is thoroughly mixed.

The mixture is then placed in a form and heated to remove the acetone. This results in a mass of powder with a homogeneous metal throughout the standard which can be removed from the form.

Such a standard can be used in XRF measurements. It is a dry sample of a suitable pharmaceutical excipient with a homogenous metal throughout.

The standard can be used in powder form or can be pressed to form a solid standard.

The method described above is relatively straightforward and hence the creation of a dry reference standard in this way is significantly easier than approaches involving organometallics. Further, the method has been shown to deliver excellent results, in particular excellent homogeneity which is important in a reference standard.

The ease with which standards can be made allows XRF standards to be made for multiple metals to check for contamination with a wide variety of metals.

In embodiments, a reference standard may have multiple elements included within it by mixing dilute preparations of more than one metal with the finely ground powder before heating.

The standards may each include a variety of elements in different concentrations so that the standards can be used for the measurement of a variety of elements.

In particular, the following groups of standards are proposed. Each group of standards includes a range of different elements at different concentrations. A first standard may include As, Cd, Hg and Pb. A second standard may include Ru, Rh, Pd, Ir or Pt, and a third standard may include Al, V, Cr, Mn, Fe, Ni, Cu, Zn or Mo.

Note that the standards are arranged such that each standard includes a variety of different concentrations of different elements and for each element the set of standards includes a variety of different concentrations.

An example standard is:

|    | Std-1 | Std-2 | Std-3 | Std-4 | Std-5 | Std-6 |
|----|-------|-------|-------|-------|-------|-------|
| Ru | 0.0   | 25.0  | 100.0 | 50.0  | 75.0  | 0.0   |
| Rh | 25.0  | 75.0  | 50.0  | 100.0 | 0.0   | 0.0   |
| Pd | 100.0 | 50.0  | 0.0   | 25.0  | 75.0  | 0.0   |
| Ir | 50.0  | 0.0   | 75.0  | 75.0  | 100.0 | 0.0   |
| Pt | 75.0  | 100.0 | 25.0  | 0.0   | 50.0  | 0.0   |

With this selection of dry reference standards, a wide range of elements may be checked for using X-ray fluorescence.

EXAMPLE

Examples were prepared using the following method.

Weigh 250 g of matrix/excipient (Cellulose, Lactose or Calcium Carbonate) onto a weighing paper using a three-figure balance and then transfer to a large glass dish. Place the lid on the dish and leave to one side.

Measure ~100 ml of acetone into a small glass beaker and ~370 ml of acetone into a measuring cylinder.

Pipette the required volume of commercially available standard solution into the ~100 ml of acetone. Use a new pipette tip for dispensing each standard solution in order to avoid contamination between liquid solutions.

After the final standard solution has been dispensed, carefully pour the ~370 ml of acetone over the matrix. Add more acetone if required. There should be enough liquid to pre-wet the material without over-saturating.

Pour the standard solution mix in acetone over the wet matrix. Whilst the beaker is inverted, squirt with acetone from a wash bottle, paying particular care to the beaker lip, where solution may still reside. Rinse the inside of the beaker three times with more acetone and add this to the wet mix.

Using a glass rod, thoroughly mix the wet material to ensure maximum dispersion of the standard solutions. Rinse the rod with acetone over the mixture, then squirt the insides of the glass dish down with acetone to wash any material back into the mix.

Place the entire sample inside a fume hood and leave until all of the acetone has evaporated (no smell of acetone remains).

Carefully stir the mixture at regular intervals with the glass rod to prevent concentrated patches forming, then wash this down with acetone over the mix.

When no traces of acetone are thought to remain, place the glass dish inside an oven set at 40° C. and leave until dried. This process usually takes 2-3 days. Once deemed sufficiently dry, transfer the contents of the glass dish onto weighing paper and then into a zip-lock bag, using the dedicated brush to aid removal of the contents if necessary.

The bag containing the standard is manipulated by hand in order to mix the contents, thus removing any potentially highly concentrated areas of matrix. Place the bag into a glove bag, along with weighing utensils and Nalgene bottles, seal and promptly fill the glove bag with nitrogen.

The powder is transferred to Nalgene 30 ml narrow neck bottles by weighing 5 g into a glass funnel weighing boat on the one-figure portable balance. Once all of the bottles have been filled, transfer the remaining excess powder into a zip-lock bag.

Wrap sealing tape around the cap and neck of each bottle. This step should be repeated for all standards. The remaining powder in the zip-lock bag is analysed using a PANalytical Epsilon3 (trade mark) spectrometer to assess the quality, including accuracy and homogeneity, of the dry reference standard produced.

The above description represents an example of the method according to the invention. Those skilled in the art will realise that many variations are possible.

For example, the exact quantities of the solvent or the identity of the solvent may be changed. Instead of acetone, water, tetrahydrofuran, propan-1-ol, propan-2-ol, methanol, ethanol, 1-4 dioxane, dimethylsulfoxide, or acetonnitrile for example may be used.

The temperatures and times indicated above may be varied as appropriate. Details of how the weighing takes place, the vessels used and the fine details of the method may be varied as appropriate.

The drying of the sample may take place at suitable temperatures and times and may be varied as long as the sample is sufficiently dry to evaporate the solvent.

Results

To verify the homogeneity and repeatability of the results, the above method was carried out for the element arsenic using a cellulose excipient.

In particular, five standards were prepared using the method above with variable amounts of arsenic.

These standards were then used to prepare a calibration line, shown in the FIGURE. The line records the measured XRF intensity (I rate corrected As/Internal ratio) against the known concentration of As in ppm. Each standard in turn was measured in an Epsilon3 XRF spectrometer and the result output. The results were fitted to a straight line which was recorded in the instrument as the calibration. The root mean square error was 2.39 ppm, the lower limit of detection ($3\sigma$) was 0.2 ppm and the detector live time for each was 120 s.

A sample with nominal 30 ppm As in excipient was then used for measurement.

Ten aliquots from the bulk sample (labelled Cell-LP-06 A to J) were taken as loose powder (5 g) samples. They were measured once (#1), then each sample was removed from the cuvette, tipped back in & reanalysed (#2) and repeated (#3). This provided three sets of ten measurements on which to perform statistical analysis. The measurements presented in the table below were analyzed using an Epsilon3 Spectrometer.

| As (ppm) | Measurement | | |
|---|---|---|---|
| Sample ID | #1 | #2 | #3 |
| Weighed target | 30.0 | 30.0 | 30.0 |
| Cell-LP-06 A | 33.4 | 32.0 | 30.7 |
| Cell-LP-06 B | 31.0 | 32.4 | 32.4 |
| Cell-LP-06 C | 32.2 | 32.1 | 31.4 |
| Cell-LP-06 D | 33.2 | 32.9 | 31.9 |
| Cell-LP-06 E | 32.2 | 31.2 | 34.4 |
| Cell-LP-06 F | 31.9 | 32.6 | 33.3 |
| Cell-LP-06 G | 32.9 | 32.9 | 35.5 |
| Cell-LP-06 H | 30.7 | 33.0 | 30.5 |
| Cell-LP-06 I | 32.8 | 31.5 | 30.6 |
| Cell-LP-06 J | 31.9 | 33.3 | 34.3 |
| Mean | 32.2 | 32.4 | 32.5 |
| St. Dev. | 0.89 | 0.68 | 1.79 |
| Rel. St. Dev. | 2.8% | 2.1% | 5.5% |

A Grubbs test was carried out on the data to determine any anomalous results. One value of the thirty measured was a value which may be considered to be an "outlier" outside the normal distribution, i.e. the value 35.5.

The samples were tested using ICP-MS, inductively coupled plasma mass spectrometry. Good reproducibility was shown and the samples passed the Students-t test, demonstrating that the samples are of good quality.

An analysis of variance (ANOVA) test was carried out. Single factor ANOVA gave the following results for the first, second and third measurements of each of the samples:

| Groups | Count | Sum | Average | Variance |
|---|---|---|---|---|
| Cell-LP-06 #1 | 10 | 322.2 | 32.22 | 0.7951 |
| Cell-LP-06 #2 | 10 | 323.9 | 32.39 | 0.4677 |
| Cell-LP-06 #3 | 10 | 325.0 | 32.50 | 3.2133 |

The second part of ANOVA compares mean squares using the null and alternate hypotheses by way of an F-Test.

In this example, there is no statistical significance (F 0.133<F crit 3.354). The probability (known as p-value) of the value of F greater than or equal to the critical value is 0.876, which is very much higher than 0.05. Accordingly, the variance within the groups is not statistically significant at the 95% confidence limit (P 0.876<0.05), therefore the null hypothesis can be accepted. In other words, the result does not suggest a significant difference between the groups.

Thus, the samples prepared using this method are good quality and have good reproducibility. In particular, the ten different 5 g samples showed good reproducibility between samples.

Thus, good dry reference samples have been prepared with good results using a method that is much less problematic and hazardous than previous approaches using organometallics.

The invention claimed is:
1. A method of manufacturing a dry reference standard for X-ray fluorescence measurements, comprising:
providing a reference sample having a known concentration of a predetermined element;
transferring the reference sample volumetrically into acetone to prepare a diluted reference standard having a concentration of 10 to 500 ppm of the predetermined element;
mixing the diluted reference standard with an excipient material in powder form;
evaporating the acetone to form a dry reference standard with the known concentration of the predetermined element homogeneously dispersed in the excipient material.

2. The method according to claim 1 wherein evaporating the acetone includes carrying out a first evaporation step at room temperature followed by a second evaporation step in an oven at an elevated temperature above 35° C.

3. The method according to claim 2 wherein the second evaporation step is carried out for a period of at least 24 hours.

4. The method according to claim 1, wherein the excipient material is lactose, cellulose or calcium carbonate or any mixture thereof.

5. The method according to claim 1, wherein providing a reference sample includes providing at least one reference sample having a known concentration of each of a plurality of elements and transferring the at least one reference sample volumetrically into a solvent to obtain a diluted reference sample having a known concentration of each of the said plurality of elements.

6. A method of providing a plurality of dry reference standards,
the method comprising providing a reference sample having a known concentration of a predetermined element;
transferring a different concentration of the reference sample volumetrically into acetone for each of the plurality of dry reference standards to prepare a plurality of diluted reference standards having a concentration of 10 to 500 ppm of the predetermined element;
mixing the diluted reference standards with an excipient material in powder form;
evaporating the acetone to form the plurality of dry reference standards with different known concentrations of the predetermined element homogeneously dispersed in the excipient material.

7. A method of calibrating X-ray fluorescence apparatus, comprising:
preparing a plurality of dry reference standards having different concentrations of a predetermined element providing a reference sample having a known concentration of the predetermined element by, for each dry reference standard, transferring the reference sample volumetrically into acetone to prepare a plurality of diluted reference standards having a concentration of 10 to 500 ppm of the predetermined element; mixing the diluted reference standards with an excipient material in powder form; and evaporating the acetone to form a dry reference standard with the known concentration of the predetermined element homogeneously dispersed in the excipient material;
measuring the X-ray fluorescence of each of the dry reference standards; and
calculating a calibration line from the measured X-ray fluorescence and the known concentrations of the predetermined element.

* * * * *